United States Patent
Nakajima

(10) Patent No.: US 9,718,211 B2
(45) Date of Patent: Aug. 1, 2017

(54) DEVICE FOR PRODUCING ABSORBENT BODY

(71) Applicant: Zuiko Corporation, Osaka (JP)

(72) Inventor: Yoshihiro Nakajima, Osaka (JP)

(73) Assignee: Zuiko Corporation, Osaka (JP)

(*) Notice: Subject to any disclaimer, the term of this patent is extended or adjusted under 35 U.S.C. 154(b) by 12 days.

(21) Appl. No.: 14/413,612

(22) PCT Filed: Jun. 27, 2013

(86) PCT No.: PCT/JP2013/067627
§ 371 (c)(1),
(2) Date: Jan. 8, 2015

(87) PCT Pub. No.: WO2014/010426
PCT Pub. Date: Jan. 16, 2014

(65) Prior Publication Data
US 2015/0190943 A1   Jul. 9, 2015

(30) Foreign Application Priority Data
Jul. 10, 2012  (JP) .................................. 2012-154345

(51) Int. Cl.
*B27N 3/04* (2006.01)
*A61F 13/49* (2006.01)
(Continued)

(52) U.S. Cl.
CPC .......... *B27N 3/04* (2013.01); *A61F 13/15617* (2013.01); *A61F 13/15658* (2013.01);
(Continued)

(58) Field of Classification Search
CPC ........................................... A61F 2013/15943
(Continued)

(56) References Cited

U.S. PATENT DOCUMENTS

| 1,980,193 | A | * | 11/1934 | Finegan | ................. | D21B 1/061 |
|---|---|---|---|---|---|---|
| | | | | | | 241/167 |
| 2003/0236510 | A1 | | 12/2003 | Yasumura et al. | | |
| 2007/0227679 | A1 | * | 10/2007 | Maruhata | ............... | D21B 1/066 |
| | | | | | | 162/20 |

FOREIGN PATENT DOCUMENTS

| CN | 1954108 A | 4/2007 |
|---|---|---|
| JP | H08-337954 A | 12/1996 |

(Continued)

OTHER PUBLICATIONS

International Preliminary Report on Patentability issued Jan. 13, 2015 in related International Patent Application No. PCT/JP2013/067627 (1 page).
Written Opinion issued Jan. 10, 2015 in related International Patent Application No. PCT/JP2013/067627 (with translation) (6 pages).
International Search Report issued in PCT/JP2013/067627 mailed on Sep. 17, 2013 (2 pages).

(Continued)

*Primary Examiner* — Matthew Daniels
*Assistant Examiner* — Kimberly A Stewart
(74) *Attorney, Agent, or Firm* — Osha Liang LLP

(57) ABSTRACT

A device for producing an absorbent body includes crushers that are each configured to crush a supplied pulp sheet into fluff pulp and that each include a plurality of rotating blades, a duct in which the fluff pulp is carried by air, and a rotating fiber stacking drum that includes an adsorbent molding section that molds the fluff pulp carried by air from the duct into an absorbent body with a desired shape. Further, the crushers are staggered in an axis direction of the rotating blades.

5 Claims, 3 Drawing Sheets

(51) Int. Cl.
*D04H 1/732* (2012.01)
*A61F 13/15* (2006.01)
*D21B 1/06* (2006.01)

(52) U.S. Cl.
CPC .............. *A61F 13/49* (2013.01); *D04H 1/732* (2013.01); *D21B 1/066* (2013.01)

(58) Field of Classification Search
USPC ........................................................ 425/82.1
See application file for complete search history.

(56) References Cited

FOREIGN PATENT DOCUMENTS

| | | | | |
|---|---|---|---|---|
| JP | 2001-309945 | * | 11/2001 | ............ A61F 3/534 |
| JP | 2004-065930 | A | 3/2004 | |
| JP | 2007-089826 | A | 4/2007 | |
| WO | 2006019100 | A1 | 2/2006 | |

OTHER PUBLICATIONS

Extended European Search Report issued in the counterpart European Patent Application No. 138173315, mailed Mar. 9, 2016 (6 pages).
Notification of the First Office Action issued in corresponding Chinese Application No. 201380036637.X, mailed on May 5, 2016 (10 pages).
Office Action issued in the counterpart Chinese Application No. 201380036637.X, mailed Nov. 28, 2016 (8 pages).

* cited by examiner

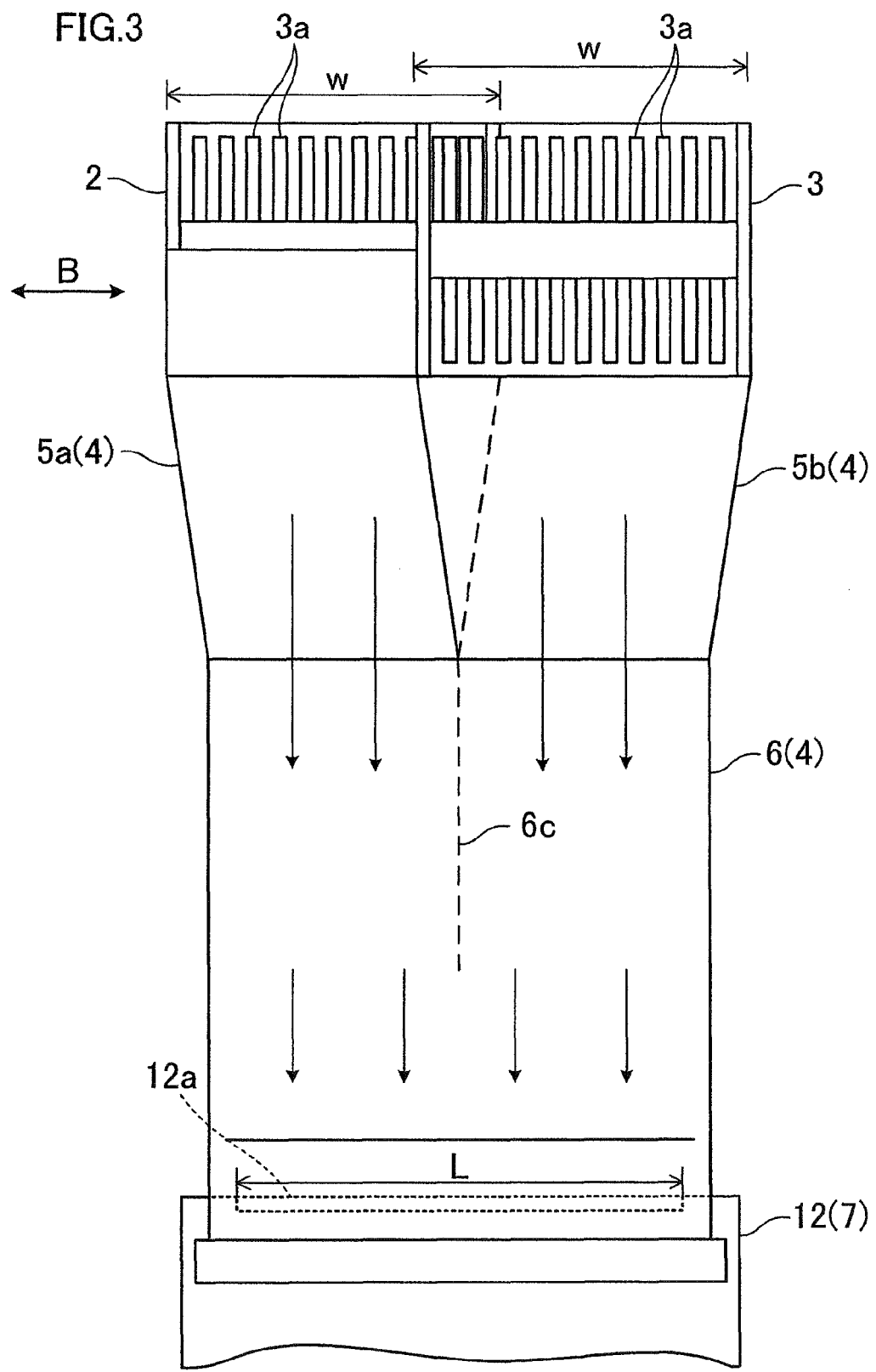

DEVICE FOR PRODUCING ABSORBENT BODY

TECHNICAL FIELD

The present invention relates to a device for producing an absorbent body used for sanitary items such as paper diapers and sanitary napkins.

BACKGROUND ART

As described in Patent Literature 1, an absorbent body with a desired shape is formed in such a way that, a pulp sheet is crushed by a crusher including a plurality of rotating blades into fluff pulp, a mixed flow is formed by carrying the fluff pulp on an air flow to a duct and at the same time supplying a water absorbing polymer in the duct to be merged with the fluff pulp carrying flow, and the mixed flow is then transported to a rotating fiber stacking drum so that the mixed flow is adsorbed and retained by an adsorbent molding section which is formed on the outer circumference of the rotating fiber stacking drum.

CITATION LIST

Patent Literature

[Patent Literature 1] Japanese Unexamined Patent Publication No. 8-337954

SUMMARY OF INVENTION

Technical Problem

In connection with the above, there is a case where an absorbent body wider than the crusher in width may be formed, provided that the direction of the axis of each rotating blades of the crusher is the width direction. In this case, a duct that widens toward the downstream, in which the width of the duct on the inlet side is arranged to be identical with the width of the crusher whereas the width of the duct on the outlet side is arranged to be identical with the width of the adsorbent molding section, may be used. This, however, is disadvantageous in that, the fluff pulp accumulated on the adsorbent molding section is irregular in width and not uniform in the width direction of the adsorbent molding section, with the result that the absorbent body is irregular in the width direction.

To solve this problem, the width of the crusher may be increased in accordance with the width of the absorbent body. Furthermore, in accordance with the increase in the width of the crusher, the width of the pulp sheet inserted into the crusher may also be increased. This, however, is disadvantageous in that, when the crusher is widened, the rotational shaft supporting the rotating blades must be long. Because such a rotational shaft bends during the crushing of the pulp sheet, the pulp sheet is not uniformly crushed. Furthermore, the manufacturing costs increase when a dedicated pulp sheet is used instead of a currently-used all-purpose pulp sheet.

One or more embodiments of the present invention provide a device that is capable of producing a wide absorbent body without causing irregularity in thickness, poor crushing, and increase in manufacturing costs.

Solution to Problem

One or more embodiments of a device for producing an absorbent body include: crushers each configured to crush a supplied pulp sheet into fluff pulp and including a plurality of rotating blades; a duct in which the fluff pulp is carried by air; and a rotating fiber stacking drum including an adsorbent molding section which molds the fluff pulp carried by air from the duct into an absorbent body with a desired shape, the crushers being staggered in an axis direction of the rotating blades.

According to this arrangement, plural crushers are disposed to be staggered in the axis direction of the rotating blades and the fluff pulp is supplied from each of the crushers. With this, the fluff pulp is accumulated evenly on the adsorbent molding section in the width direction thereof, even if the absorbent body to be formed is wider than each of the crushers. As a result, the thickness of the absorbent body molded by the adsorbent molding section is made uniform in the width direction. In so doing, because it is unnecessary to increase the width of the crusher or the width of the pulp sheet, it is possible to employ an all-purpose pulp sheet and such a pulp sheet is evenly crushed. It is therefore possible to form a wide absorbent body without causing irregularity in thickness, poor crushing, and increase in manufacturing costs. It is noted that the widths above indicate the sizes in the axis direction.

In addition to the above, one or more embodiments of the device for producing the absorbent body may be arranged such that the duct includes: upstream ducts which are provided for the respective crushers, to each of which a stream of the fluff pulp is charged from the corresponding crusher; and a downstream duct which is connected to outlets of the respective upstream ducts and in which the streams of the fluff pulp carried by air in the respective upstream ducts are merged and carried by air toward the rotating fiber stacking drum. According to this arrangement, the streams of the fluff pulp carried by air in the respective upstream ducts are merged in the downstream duct and then carried by air toward the rotating fiber stacking drum. As the flow of the fluff pulp carried by air toward the adsorbent molding section is made uniform in the width direction, the thickness of the absorbent body is even in the width direction.

In addition to the above, one or more embodiments of the device for producing the absorbent body may be arranged such that the neighboring crushers partly overlap each other in the axis direction. According to this arrangement, because the neighboring crushers are arranged to partly overlap each other in the axis direction, the fluff pulp supplied from the crushers is uninterruptedly accumulated on the adsorbent molding section in the width direction thereof. Furthermore, the utilization range of known crushers which are each narrower than the adsorbent molding section but which are longer than the adsorbent molding section in total width is further extended, as the range of the overlap of the neighboring crushers in the axis direction is adjusted in accordance with the widths of these crushers.

In addition to the above, one or more embodiments of the device for producing the absorbent body may be arranged such that when the axis direction is a width direction, a total width of the widths of the crushers is longer than the width of the adsorbent molding section, and the width of the duct narrows from the crusher side to the rotating fiber stacking drum side. According to this arrangement, because the total width of the widths of the crushers is arranged to be longer than the width of the adsorbent molding section and the width of the duct is arranged to narrow from the crusher side toward the rotating fiber stacking drum side, the fluff pulp supplied from the crushers is evenly accumulated on the adsorbent molding section in the width direction thereof.

Furthermore, because the total width of the widths of the crushers is arranged to be longer than the width of the adsorbent molding section, it is possible to extend the utilization range of known crushers each of which is narrower than the adsorbent molding section in width but which are longer than the adsorbent molding section in the total width.

In addition to the above, one or more embodiments of the device for producing the absorbent body may be arranged such that the crushers form a single line in the axis direction, and when the axis direction is a width direction, a total width of the widths of the crushers is identical with the width of the duct and with the width of the adsorbent molding section. According to this arrangement, the crusher are arranged to form a single line in the axis direction to cause the total width of the widths of the crushers to be identical with the width of the duct and with the width of the adsorbent molding section. With this, the fluff pulp supplied from the crushers is evenly accumulated on the adsorbent molding section in the width direction thereof.

Advantageous Effect of Invention

One or more embodiments of the device for producing an absorbent body make it possible to form a wide absorbent body without causing irregularity in thickness, poor crushing, and increase in manufacturing costs.

BRIEF DESCRIPTION OF DRAWINGS

FIG. 3 is a profile when
FIG. 1 is viewed in the direction C.

DESCRIPTION OF EMBODIMENT

Figure 1:
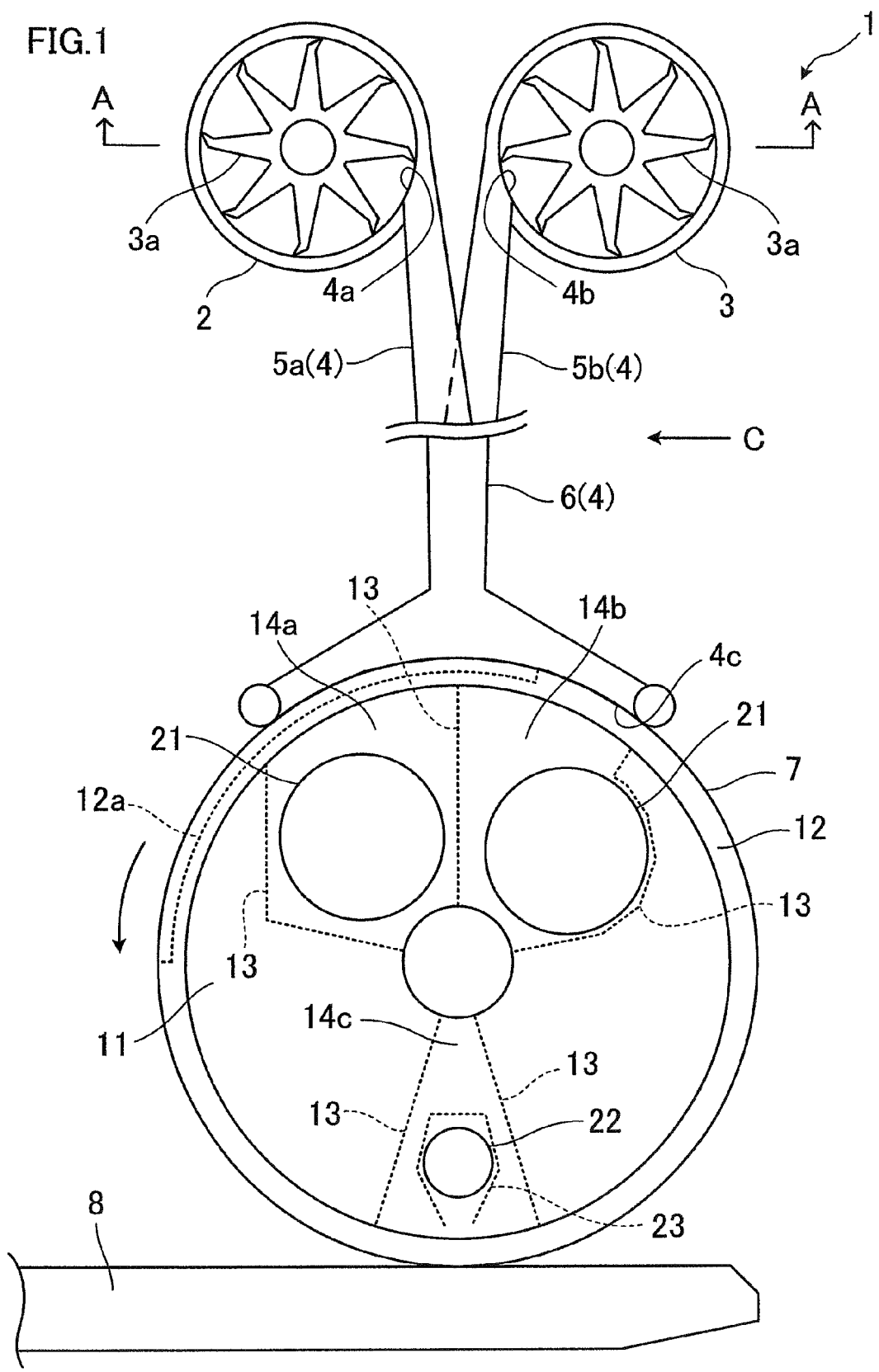
FIG. 1 is a schematic view of a device for producing an absorbent body.

The following will describe a preferred embodiment of the present invention with reference to figures.
(Structure of Device for Producing Absorbent Body)
As shown in FIG. 1, a device for producing absorbent body 1 of the present embodiment includes two crushers 2 and 3 which are configured to crush a material pulp sheet into fluff pulp, a duct 4 to which the fluff pulp is carried on an air flow (i.e., to which the fluff pulp is carried by air), a rotating fiber stacking drum 7 configured to mold the fluff pulp into an absorbent body with a desired shape, and a vacuum conveyor 8 configured to receive the absorbent body molded by the rotating fiber stacking drum 7.

The crusher 2 is attached to a one-end-side opening 4a of the duct 4. The crusher 3 is attached to a one-end-side opening 4b of the duct 4. To each of the crushers 2 and 3, a pulp sheet is supplied from a pair of feed rollers (not illustrated). On the roll surfaces of the crushers 2 and 3, a plurality of rotating blades 3a are provided to finely crush the supplied pulp sheets. The fluff pulp formed by crushing the pulp sheets is, inside the duct 4, carried on an air flow generated in the duct 4, toward the rotating fiber stacking drum 7.

In connection with the above, the duct 4 includes upstream ducts 5a and 5b provided for the respective crushers 2 and 3 and a downstream duct 6 connected to the outlets of the respective upstream ducts 5a and 5b. Into the upstream duct 5a, the fluff pulp is charged from the crusher 2. Into the upstream duct 5b, the fluff pulp is charged from the crusher 3. The streams of the fluff pulp carried by air in the respective upstream ducts 5a and 5b are merged in the downstream duct 6, and then carried by air toward the rotating fiber stacking drum 7.

To a desired position between the ends of the duct 4, a water absorbing polymer supply pipe (not illustrated) is attached. Through this water absorbing polymer supply pipe, the water absorbing polymer is supplied into the duct 4. As the water absorbing polymer supplied to the duct 4 spreads inside the duct 4, a mixed flow in which the fluff pulp and the water absorbing polymer are evenly mixed is generated in the duct 4. This mixed flow is carried by air toward the rotating fiber stacking drum 7.

The rotating fiber stacking drum 7 includes a rotatable cylinder 12 and a pair of side walls 11 which are provided not to be rotatable and close the respective ends of the cylinder 12. The rotating fiber stacking drum 7 is pressed onto and connected to an other-end-side opening 4c of the duct 4 so that the cylinder 12 is rotatable. At least one of the paired side walls 11 is connected to two suction ducts 21 and a single air supply duct 22. The numbers of the suction ducts 21 and the air supply duct 22 are not limited to the above, and the number of the suction ducts 21 may be three or more, for example.

On the outer circumference of the cylinder 12, an adsorbent molding section 12a is formed. This adsorbent molding section 12a corresponds to the shape of an absorbent body to be formed, allows air to pass therethrough, and is made of a metal mesh. As this adsorbent molding section 12a adsorbs and retains the mixed flow of the fluff pulp and the water absorbing polymer, an absorbent body with a desired shape is formed. The cylinder 12 is continuously rotated at a regular speed in the direction indicated by the arrow, by an unillustrated driving means.

The inside of the rotating fiber stacking drum 7 is partitioned by a plurality of partition plates 13 into a plurality of regions. More specifically, the inside of the rotating fiber stacking drum 7 is partitioned into two sucking regions 14a and 14b that are open upward and oppose the other-end-side opening 4c of the duct 4, a single discharge region 14c which is open downward and oppose the vacuum conveyor 8, and another region. The circumferential length of the sucking region 14a is half as long as the circumferential length of the other-end-side opening 4c. The circumferential length of the sucking region 14b is half as long as the circumferential length of the other-end-side opening 4c.

Each of the two neighboring sucking regions 14a and 14b is connected to one end of the suction duct 21 which has the other end that is connected to a sucking device (not illustrated) such as a sucking fan. As the sucking device sucks the air in the sucking region 14a through the suction duct 21, the pressure inside the sucking region 14a is kept to be negative. In a similar manner, as the sucking device sucks the air in the sucking region 14b through the suction duct 21, the pressure inside the sucking region 14b is kept to be negative.

In the structure above, when the air in each of the sucking region 14a and the sucking region 14b is sucked through the suction duct 21 so that the pressures inside the sucking region 14a and the sucking region 14b are kept to be negative, an air flow from the outer circumference side of the adsorbent molding section 12a toward the inside of the cylinder 12 is generated in the duct 4 having the other-end-side opening 4c that opposes the two sucking regions 14a and 14b. By this air flow, the mixed flow of the fluff pulp and the water absorbing polymer is carried by air in the duct 4 toward the rotating fiber stacking drum 7.

It is noted that, in accordance with the length of the absorbent body to be formed (i.e., the circumferential length of the adsorbent molding section 12a), the inside of one or both of the sucking region 14a and the sucking region 14b is arranged to be negative in pressure. That is to say, when the absorbent body to be formed is relatively short, the inside of one of the sucking region 14a and the sucking region 14b is arranged to be negative in pressure. On the other hand, when the absorbent body to be formed is relatively long, the inside of the sucking region 14a and the inside of the sucking region 14b are both arranged to be negative in pressure. In this way, the absorbent body with the desired length is formed.

In addition to the above, to the discharge region 14c, the other end of the air supply duct 22 which has one end connected to an air supplier (not illustrated) such as a compressor is connected. As the air supplier supplies compressed air into the discharge region 14c through the air supply duct 22, the inside of the discharge region 14c is arranged to be positive in pressure.

In addition to the above, in the discharge region 14c, a discharge guide 23 is provided to guide the compressed air in such a way that the compressed air in the discharge region 14c is discharged from the inside of the cylinder 12 to the outer circumference side of the adsorbent molding section 12a. This discharge guide 23 is formed to be U-shaped in cross section and open only downward in the figure, in order to guide the compressed air toward the vacuum conveyor 8.

The other end of the air supply duct 22 penetrates an opening of the side wall 11 and is connected to a side-wall opening of the discharge guide 23. In this way, the air supply duct 22 is connected to the inside of the discharge guide 23. The width of the discharge guide 23 (i.e., the length in the direction orthogonal to the plane of the figure) is arranged to be longer than the width of the adsorbent molding section 12a.

In this structure, as the compressed air is supplied into the discharge region 14c through the air supply duct 22 and hence the inside of the discharge region 14c becomes positive in pressure, the compressed air guided to the discharge guide 23 is discharged from the inside of the cylinder 12 to the outer circumference side of the adsorbent molding section 12a. In other words, the compressed air guided to the discharge guide 23 is discharged toward the vacuum conveyor 8 that opposes the discharge region 14c. On account of a pressing force of this compressed air and a later-described sucking force of the vacuum conveyor 8, the absorbent body in the adsorbent molding section 12a is passed to the vacuum conveyor 8.

The vacuum conveyor 8 contacts with a part of the rotating fiber stacking drum 7 via amount (not illustrated) which is provided for supporting the absorbent body. The vacuum conveyor 8 is provided with a sucking device (not illustrated) generating a sucking force, at a part of the inside of the vacuum conveyor 8 which part opposes a part contacting with the rotating fiber stacking drum 7. The absorbent body formed at the adsorbent molding section 12a of the cylinder 12 of the rotating fiber stacking drum 7 is passed to the surface of the mount by the pressing force of the compressed air discharged toward the vacuum conveyor 8 and the sucking force of the vacuum conveyor 8.

(Crushers)

Figure 2:
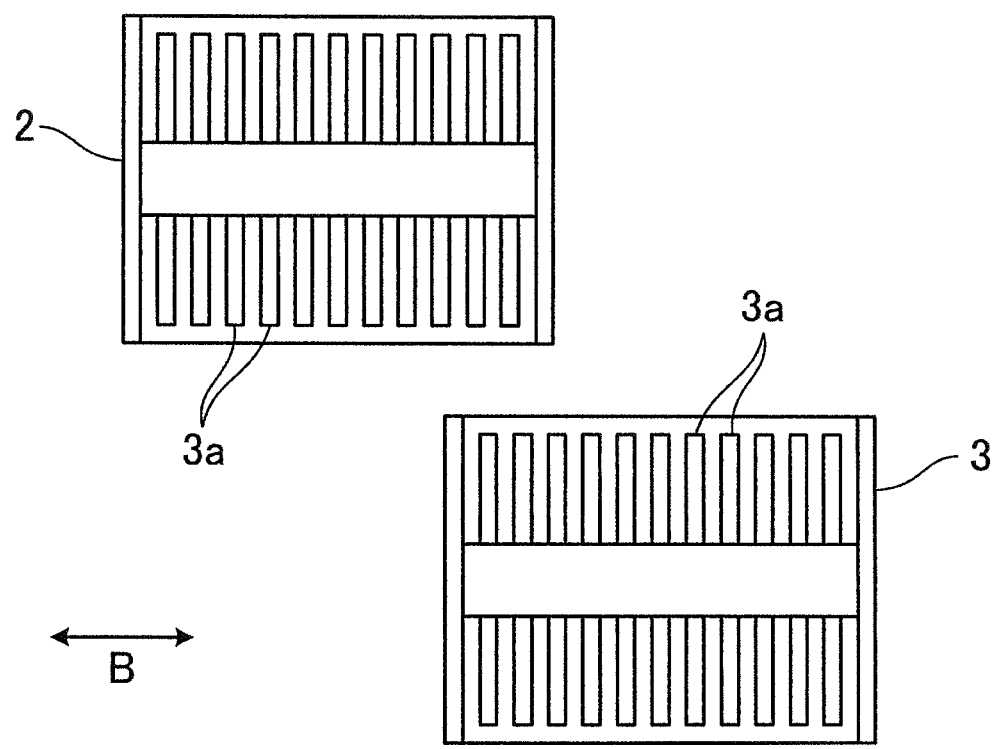
FIG. 2 is a cross section taken at the A-A line in FIG. 1.

As shown in FIG. 2 which is a cross section taken at the A-A line in FIG. 1, the crusher 2 and the crusher 3 which neighbor each other are in parallel to each other in the axis direction B of the rotating blades 3a, and are lined up in the direction orthogonal to the axis direction B. Furthermore, the crusher 2 and the crusher 3 neighboring each other are partly overlapped with each other in the axis direction B. As such, the two crushers 2 and 3 are staggered in the axis direction B. It is noted that the number of the crushers is not limited to two, and may be three or more.

As shown in FIG. 3 which is a profile when FIG. 1 is viewed in the direction C, provided that the axis direction B of the rotating blades 3a is a width direction, the width w of each of the crushers 2 and 3 is shorter than the width L of the adsorbent molding section 12a (w<L). In other words, in the present embodiment, the absorbent body which is wider than each of the crushers 2 and 3 is formed.

In regard to the above, the total width (2w) of the widths w of the crushers 2 and 3 is longer than the width L of the adsorbent molding section 12a (2w>L). The width of the duct 4 narrows from the crushers 2 and 3 side toward the rotating fiber stacking drum 7 side.

In this structure, the fluff pulp from the crusher 2 is charged into the upstream duct 5a, whereas the fluff pulp from the crusher 3 is charged into the upstream duct 5b. Thereafter, the streams of the fluff pulp carried by air in the respective upstream ducts 5a and 5b are merged in the downstream duct 6 and then carried by air toward the rotating fiber stacking drum 7.

In regard to the above, because the crushers 2 and 3 neighboring each other are arranged to partly overlap each other in the axis direction B, the fluff pulp supplied from the crushers 2 and 3 is uninterruptedly accumulated on the adsorbent molding section 12a in the width direction thereof. Furthermore, because the total width (2w) of the widths of the crushers 2 and 3 is arranged to be longer than the width L of the adsorbent molding section 12a and the width of the duct 4 is arranged to narrow from the crushers 2 and 3 side toward the rotating fiber stacking drum 7 side, the fluff pulp supplied from the crushers 2 and 3 is evenly accumulated on the adsorbent molding section 12a in the width direction thereof. This causes the thickness of the absorbent body molded by the adsorbent molding section 12a to be even in the width direction. In this connection, because it is unnecessary to increase the width of the crusher or the width of the pulp sheet, it is possible to employ an all-purpose pulp sheet and such a pulp sheet is evenly crushed.

In addition to the above, because the total width (2w) of the widths w of the crushers 2 and 3 is arranged to be longer than the width L of the adsorbent molding section 12a, it is possible to extend the utilization range of known crushers each of which is shorter than the adsorbent molding section 12a in width but which are longer than the adsorbent molding section 12a in the total width. Furthermore, the utilization range of the known crushers is further extended as the range of the overlap of the neighboring crushers in the axis direction B is adjusted in accordance with the widths of these crushers.

(Duct)

As shown in FIG. 3, the duct 4 includes the upstream duct 5a to which the fluff pulp is charged from the crusher 2, the upstream duct 5b to which the fluff pulp is charged from the crusher 3, and the downstream duct 6 connected to the outlets of the respective upstream ducts 5a and 5b.

Provided that the axis direction B is the width direction, the width of the inlet of the upstream duct 5a is identical with the width w of the crusher 2, and the width of the outlet of the upstream duct 5a is half as long as the width L of the adsorbent molding section 12a. In a similar manner, the width of the inlet of the upstream duct 5b is identical with the width w of the crusher 3, and the width of the outlet of the upstream duct 5b is half as long as the width L of the adsorbent molding section 12a. As such, the upstream duct 5a and the upstream duct 5b are shaped to narrow from the crushers 2 and 3 side toward the downstream duct 6 side. Furthermore, the width of the downstream duct 6 is identical with the width L of the adsorbent molding section 12a between the inlet and the outlet.

In this structure, streams of the fluff pulp carried by air in the upstream ducts 5a and 5b are merged in the downstream duct 6 and then carried by air toward the rotating fiber stacking drum 7. As the flow of the fluff pulp carried by air toward the adsorbent molding section 12a is made uniform in the width direction, the thickness of the absorbent body is even in the width direction.

In addition to the above, inside the downstream duct 6, a partition plate 6c is provided at the center in the width direction to separate the flow coming from the upstream duct 5a from the flow coming from the upstream duct 5b. The upper end of the partition plate 6c is at the inlet of the downstream duct 6, whereas the lower end of the partition plate 6c is above the outlet of the downstream duct 6. On account of this partition plate 6c, the flow coming from the upstream duct 5a and the flow coming from the upstream duct 5b are straightened and run toward the adsorbent molding section 12a as a flow which is uniform in the width direction.

(Effects)

As described above, in the device for producing the absorbent body 1 of the present embodiment, plural crushers 2 and 3 are disposed to be staggered in the axis direction B of the rotating blades 3a and the fluff pulp is supplied from each of the crushers 2 and 3. With this, the fluff pulp is accumulated evenly on the adsorbent molding section 12a in the width direction thereof, even if the absorbent body to be formed is wider than each of the crushers 2 and 3. As a result, the thickness of the absorbent body molded by the adsorbent molding section 12a is made uniform in the width direction. In so doing, because it is unnecessary to increase the width of the crusher or the width of the pulp sheet, it is possible to employ an all-purpose pulp sheet and such a pulp sheet is evenly crushed. It is therefore possible to form a wide absorbent body without causing irregularity in thickness, poor crushing, and increase in manufacturing costs.

In addition to the above, the streams of the fluff pulp carried by air in the respective upstream ducts 5a and 5b are merged in the downstream duct 6 and then carried by air toward the rotating fiber stacking drum 7. As the flow of the fluff pulp carried by air toward the adsorbent molding section 12a is made uniform in the width direction, the thickness of the absorbent body is even in the width direction.

In addition to the above, because the neighboring crushers 2 and 3 are arranged to partly overlap each other in the axis direction B, the fluff pulp supplied from the crushers 2 and 3 is uninterruptedly accumulated on the adsorbent molding section 12a in the width direction thereof. Furthermore, the utilization range of known crushers which are each narrower than the adsorbent molding section 12a but which are longer than the adsorbent molding section 12a in total width is further extended, as the range of the overlap of the neighboring crushers in the axis direction B is adjusted in accordance with the widths of these crushers.

Furthermore, because the total width of the widths of the crushers 2 and 3 is arranged to be longer than the width of the adsorbent molding section 12a and the width of the duct 4 is arranged to narrow from the crushers 2 and 3 side toward the rotating fiber stacking drum 7 side, the fluff pulp supplied from the crushers 2 and 3 is evenly accumulated on the adsorbent molding section 12a in the width direction thereof. Furthermore, because the total width of the widths of the crushers 2 and 3 is arranged to be longer than the width of the adsorbent molding section 12a, it is possible to extend the utilization range of known crushers each of which is narrower than the adsorbent molding section 12a in width but which are longer than the adsorbent molding section 12a in the total width.

(Modifications)

As a modification of the present embodiment, as shown in FIG. 3, the crusher 2 and the crusher 3 do not overlap each other at all in the axis direction B, and form a single line in the axis direction B. Furthermore, the total width (2w) of the widths w of the crushers 2 and 3 may be identical with the width of the duct 4 and the width L of the adsorbent molding section 12a. In other words, between the inlet and the outlet, the width of each of the upstream ducts 5a and 5b is arranged to be half as long as the width L of the adsorbent molding section 12a (i.e., identical with the width w of each of the crushers 2 and 3). Also in this structure, the fluff pulp supplied from the crushers 2 and 3 is evenly accumulated on the adsorbent molding section 12a in the width direction thereof. In this case, instead of the duct 4 having two inlets, a straight duct which has a single inlet and is even in width between the inlet and the outlet may be used.

Modifications of Present Embodiment

The above embodiment thus described solely serves as a specific example of the present invention, and the present invention is not limited to such an example. Specific structures of various means and the like may be suitably designed or modified. Further, the effects of the present invention described in the above embodiment are not more than examples of most preferable effects achievable by the present invention. The effects of the present invention are not limited to those described in the embodiments described above.

For example, in the arrangement shown in FIG. 3, the crusher 2 and the crusher 3 may be separated from each other in the axis direction B. In this case, the duct 4 is Y-shaped such that the upstream duct 5a and the upstream duct 5b are separated from each other in the axis direction B.

REFERENCE SIGNS LIST

1: DEVICE FOR PRODUCING ABSORBENT BODY
2, 3: CRUSHER
3a: ROTATING BLADE
4: DUCT
4a, 4b: ONE-END-SIDE OPENING
4c: OTHER-END-SIDE OPENING
5a, 5b: UPSTREAM DUCT
6: DOWNSTREAM DUCT
6c: PARTITION PLATE
7: ROTATING FIBER STACKING DRUM
8: VACUUM CONVEYOR
11: SIDE WALL
12: CYLINDER
12a: ADSORBENT MOLDING SECTION
13: PARTITION PLATE
14a, 14b: SUCKING REGION
14c: DISCHARGE REGION
21: SUCTION DUCT
22: AIR SUPPLY DUCT
23: DISCHARGE GUIDE

The invention claimed is:

1. A device for producing an absorbent body, comprising:
   crushers that are each configured to crush a supplied pulp sheet into fluff pulp and that each include a plurality of rotating blades;
   a duct in which the fluff pulp is carried by air; and
   a rotating fiber stacking drum that includes an adsorbent molding section that molds the fluff pulp carried by air from the duct into an absorbent body with a desired shape,
   wherein the crushers are parallel to each other, and are staggered in an axis direction of the rotating blades, and
   wherein the pulp sheet is supplied to each of the crushers, and
   wherein, when the axis direction is in parallel to a width direction of the absorbent molding section, the width of the absorbent molding section is longer than a width of each of the crushers.

2. The device according to claim 1, wherein the duct includes:
   upstream ducts that are each provided for a corresponding crusher, wherein a stream of the fluff pulp is charged from the corresponding crusher to each of the upstream ducts; and
   a downstream duct that is connected to outlets of the upstream ducts and in which the streams of the fluff pulp carried by air in the upstream ducts are merged and carried by air toward the rotating fiber stacking drum.

3. The device according to claim 1, wherein neighboring crushers partly overlap each other in the axis direction.

4. The device according to claim 1,
   wherein when the axis direction is a width direction, a total width of the widths of the crushers is longer than the width of the adsorbent molding section, and
   wherein the width of the duct narrows from the crusher side to the rotating fiber stacking drum side.

5. The device according to claim 1,
   wherein the crushers form a single line in the axis direction, and
   wherein when the axis direction is a width direction, a total width of the widths of the crushers is identical with the width of the duct and with the width of the adsorbent molding section.

* * * * *